United States Patent [19]

Campbell et al.

[11] Patent Number: 5,013,864

[45] Date of Patent: May 7, 1991

[54] PROCESS FOR PREPARATION OF α-ALKOXY ACETIC ACIDS AND THEIR SALTS

[75] Inventors: Arthur L. Campbell, Glenview; Richard A. Mueller, Glencoe; John S. Ng, Chicago; Richard A. Partis, Evanston, all of Ill.

[73] Assignee: G. D. Searle & Co., Chicago, Ill.

[21] Appl. No.: 447,766

[22] Filed: Dec. 8, 1989

[51] Int. Cl.$^5$ ............................................. C07C 51/02
[52] U.S. Cl. ..................... 562/426; 562/465; 562/469; 562/471; 562/472
[58] Field of Search ............... 562/426, 469, 465, 471, 562/472

[56] References Cited

U.S. PATENT DOCUMENTS

| | | | |
|---|---|---|---|
| 3,255,241 | 6/1966 | Schultz et al. | 562/426 |
| 3,918,899 | 11/1975 | Perrier et al. | 8/120 |
| 4,711,903 | 12/1987 | Mueller et al. | 562/430 X |
| 4,755,524 | 7/1988 | Mueller et al. | 562/430 X |
| 4,804,777 | 2/1989 | Summer et al. | 562/421 |

OTHER PUBLICATIONS

Fuson et al., Organic Synthesis Collected Volumes, 2: 260-262 (1943).

*Primary Examiner*—Jose G. Dees
*Assistant Examiner*—Vera C. Clarke
*Attorney, Agent, or Firm*—Mary Jo Kanady; Paul D. Matukaitis

[57] ABSTRACT

A process for producing an α-alkoxy acetic acids and salts thereof which comprises reacting an alcohol of the formula R—OH wherein R is alkyl, substituted alkyl, or cycloalkyl, or cycloalkyl alkyl with a base in an aprotic organic solvent to give an alkoxide followed by removal of the organic solvent and reaction of the alkoxide with a salt of a monohaloacetic acid in a polar aprotic solvent such as DMSO to give the corresponding alkoxyacetate salt which then may be recovered or may optionally be converted to the corresponding acid by contacting the alkoxy acetate salt with an acid.

24 Claims, No Drawings

PROCESS FOR PREPARATION OF α-ALKOXY ACETIC ACIDS AND THEIR SALTS

BACKGROUND OF THE INVENTION (a) Field of the Invention

The present invention relates to a novel one pot process for the preparation of an α-alkoxy acetic acid having the general formula

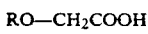

RO—CH$_2$COOH or a salt thereof, wherein R can be straight or branched chain alkyl, substituted alkyl, cycloalkyl which may optionally be substituted, cycloalkyl alkyl in which the cycloakyl may optionally be substituted or a group of the formula

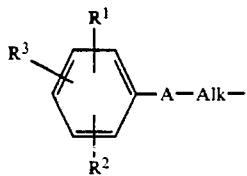

wherein R$^1$, R$^2$ and R$^3$ can be the same or different and can be hydrogen, alkyl, alkoxy, halo, phenyl, substituted phenyl, or hydroxy; A can be sulfur, oxygen, or —CH$_2$—; and Alk is straight or branched chain alkylene; which comprises reacting an alcohol of the formula

R—OH wherein R is defined as above, with a suitable base in an aprotic organic solvent to generate an alkoxide anion, removal of the organic solvent, and coupling of the alkoxide anion with a salt of a monohaloacetic acid in an aprotic polar solvent such as dimethyl sulfoxide (DMSO) to give the acid salt which can optionally be reacted with acid to give the α-alkoxy acetic acid product.

This process has the advantages of providing a high yield of product and being able to be conducted in one pot thus providing a guicker, more efficient and less costly synthesis. The process of the present invention permits the unexpectedly efficient and convenient preparat of α-alkoxy acetic acids in improved overall yield and purity and is especially useful for preparing phenylthio-α-alkoxy acetic acids.

(b) Prior Art

U.S. Pat. No. 4,711,903 and U.S. Pat. No. 4,755,524 disclose a method of preparing a [2-[[3,5-bis(1,1 dimethylethyl)-4 hydroxyphenyl]thio]alkoxy]acetic acid from a 2,6-bis (1,1-dimethylethyl)-4-[(2-hydroxyalkyl) thio]phenol by a process in which chloroacetic acid is added to the alcohol in t-butyl alcohol which is a protic solvent, then potassium tert-butoxide is added, and the mixture is refluxed. This method gives yields of less than 25% and thus is not a very efficient process.

U.S Pat. No. 4,804,777 discloses a process for the preparation of an aryloxy acetic acid by oxidation of an aryloxyethanol in an agueous alkaline reaction medium at a temperature in the range of 0° C. to the boiling point of the reaction medium in the presence of a catalytic amount of a catalyst comprised of palladium, silver, and optionally antimony, and carbon to form the corresponding alkali metal ester and contacting the alkali metal with a mineral acid.

U.S. Pat. No. 3,918,899 discloses a method of preparing carboxymethylated cottons in non-aqueous media by reacting anhydrous sodium cellulosate with a salt of a monochloroacetate in an anhydrous DMSO solution. R. C. Fuson and B. H. Wojcik, *ORGANIC SYNTHESIS COLLECTED VOLUMES,* 2:260–262(1943) discloses a three-step method for preparing ethoxyacetic acid from ethanol which is the substrate and the solvent (protic solvent).

SUMMARY OF THE INVENTION

The present invention relates to a process for preparing an α-alkoxy acetic acid of formula I

RO—CH$_2$COOH     (I)

or a salt thereof, wherein R is straight or branched chain alkyl which can optionally be substituted, cycloalkyl which can optionally be substituted, cycloalkyl alkyl in which the cycloalkyl group can optionally be substituted; or a group of the formula

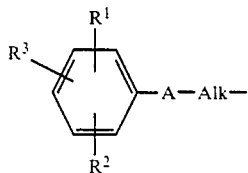

wherein R$^1$, R$^2$ and R$^3$ can be the same or different and can be hydrogen, alkyl, lower alkoxy, halo, phenyl, substituted phenyl, or hydroxy; A can be sulfur, oxygen, or —CH$_2$—; and Alk can be straight or branched chain lower alkylene; which comprises:

(a) reacting a compound of the formula

R—OH     (II)

wherein R is defined as hereinbefore with a base in an aprotic organic solvent to form an alkoxide (b) removing the organic solvent;

(c) reacting the alkoxide with a salt of a monohaloacetic acid in an aprotic polar solvent to give an alkoxyacetate salt; and (d) optionally reacting the alkoxyacetate salt with an acid to give the α-alkoxy acetic acid of formula I.

DETAILED DESCRIPTION OF THE INVENTION

The present invention relates to a process for preparing an α-alkoxy acetic acid of the formula (I)

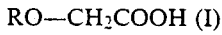

RO—CH$_2$COOH (I)

or a salt thereof, wherein R is straight or branched chain alkyl, substituted alkyl, cycloalkyl, substituted cycloalkyl, cycloalkyl alkyl, substituted cycloalkyl alkyl or a group of the formula

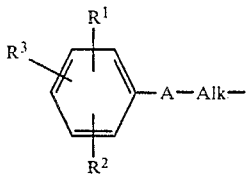

wherein $R^1$, $R^2$ and $R^3$ can be the same or different and can be hydrogen, alkyl of 1 to 10 carbon atoms, alkoxy of 1 to 4 carbon atoms halo, phenyl, substituted phenyl, or hydroxy; A can be sulfur, oxygen, or —CH$_2$—; and Alk can be straight or branched chain alkylene having from 2 to 6 carbon atoms; which comprises:

(a) reacting a compound of the formula

R—OH (II)

wherein R is defined as hereinbefore with a base in an aprotic organic solvent to form an alkoxide;

(b) removing the organic solvent; and (c) reacting the alkoxide with a salt of a monohaloacetic acid in an aprotic polar solvent to give an acetate salt which can be recovered as the salt or can optionally be reacted with an organic acid or mineral acid to give the acid product.

The process of the present invention can be conducted in one pot, thus fewer steps are required to produce the product. The process provides higher overall yields with fewer purification procedures being needed. Another advantage is that in this process the monohaloacetic acid salt does not react with the sulfur to give a sulfonium salt in those compounds wherein A is sulfur.

If the α-alkoxy acetic acid salt is desired it can be recovered as the product or optionally it can be reacted with an acid to give the α-alkoxy acetic acid as the final product.

The present invention also relates to a process for preparing a compound of the formula (III)

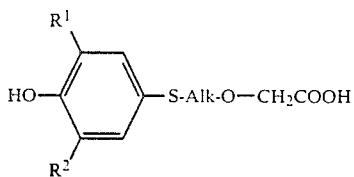

or a salt thereof, wherein $R^1$ and $R^2$ can be the same or different and can be alkyl of 1 to 10 carbon atoms, halo, phenyl, or substituted phenyl; and Alk is straight or branched chain alkylene having 2 to 6 carbon atoms; which comprises:

(a) reacting a compound of the formula

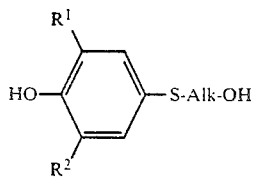

wherein $R^1$, $R^2$ and Alk are defined as hereinbefore with a base in an aprotic organic solvent to form an alkoxide;

(b) removing the organic solvent;

(c) reacting the alkoxide with a salt of a monohaloacetic acid in a polar aprotic solvent to give an alkoxy acetate salt; and (d) optionally reacting the alkoxy acetate salt with an acid to give the product of formula III.

The process of the present invention is particularly useful for preparing compounds of Formula III wherein $R^1$ and $R^2$ represent tert-alkyl.

In a preferred embodiment the process of the present invention can be used to prepare a compound of the formula

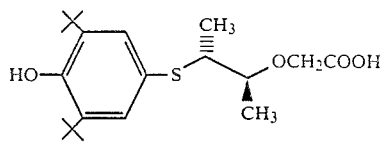

or Salt thereof, by (a) reacting a compound of the formula

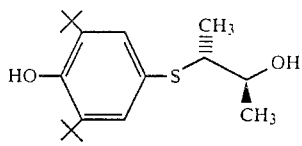

with a base such as sodium hydride in an aprotic organic solvent such as tetrahydrofuran to form an alkoxide of the formula

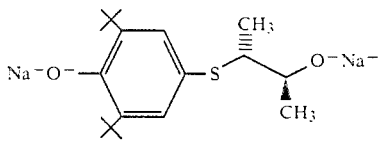

(b) removing the organic solvent;

(c) reacting the alkoxide with a salt of a monohaloacetic acid, such as monochloroacetic acid, in a polar aprotic solvent, such as DMSO, to form an alkoxy acetate salt; and (d) reacting the alkoxy acetate salt with a mineral acid or organic acid to give the product.

Aprotic organic solvents suitable for use in the present invention include but are not limited to tetrahydrofuran (THF), ethers such as ethyl ether, t butylmethyl ether, diisopropyl ether, and dioxane.

Polar aprotic solvents suitable for use in the present invention include but are not limited to dimethyl sulfoxide (DMSO), dimethylformamide (DMF), hexamethylphosphoramide (HMPA), sulfolane, dimethyl sulfone and tetramethylurea. Preferred solvents are dipolar aprotic solvents such as DMSO.

Monohaloacetic acid salts suitable for use in the present invention include but are not limited to the sodium, potassium, lithium, and cesium salts of monochloroacetic acid, monobromoacetic acid and monoiodoacetic acid.

Suitable mineral acids and organic acids for acidifying the alkoxy acetate to the acid include but are not limited to hydrochloric acid, hydrobromic acid, hydrofluoric acid, sulfuric acid, nitric acid, acetic acid, trifluoroacetic acid, methanesulfonic acid, trifluoromethanesulfonic acid and phosphoric acid.

Suitable bases for reacting with the alcohol include but are not limited to sodium hydride, potassium hydride, calcium hydride, alkyllithiums, lithium dialkylamides, lithium bis (tri methylsilyl) amide, sodium bis (tri methylsilyl) amide, and potassium bis (tri methylsilyl) amide. The reaction of the alcohol and base can be conducted over a broad temperature range, preferably from about −50° C. to about 50° C. and most preferably from about −15° C. to about 30° C.

The relative amounts of reactants used in the process can vary. Preferably an excess of base is reacted with the alcohol. In general the mole ratio of base to alcohol can be about 3 moles of base to about 1 mole of alcohol, preferably about 1.1 mole of base to about 1.0 moles of alcohol or alcohol equivalent such as an additional —OH group. In general, an excess of monohaloacetic acid salt is reacted with the alkoxide although the reaction can be conducted as a 1:1 molar ratio. Preferably, about 1.5 moles of monohaloacetic acid salt is reacted with the alkoxide intermediate.

The reactiOn to generate the alkoxide ion in the present process can be conducted over a broad temperature range, preferably from about −50° C. to about 50° C. and most preferably from about −15° C. to about 30° C.

The reaction of the alkoxide with a salt of a monohaloacetic acid may be conducted over a broad temperature range, preferably from about 0° C. to about 50° C. with about 10° C. to about 30° C. most preferred. The alkoxy acetate salt can be acidified to the acid over a broad temperature range, preferably from about 0° C. to about 50° C.

The term "alkyl", as used herein, refers to straight or branched chain alkyl groups having from 1 to 10 carbon atoms, inclusive, i.e., methyl, ethyl, n propyl, iso-propyl, n butyl, sec-butyl, tert-butyl, n-pentyl, 2-methylbutyl, 2,2 dimethylbutyl, n hexyl, and the like.

When R in Formula I is alkyl it may optionally be substituted by one or more substituents selected from the group consisting of phenyl, phenylthio, phenyloxy, substituted phenyl, alkoxy, cycloalkyl, aryloxy, and arylthio.

The term "lower alkylene", as used herein, refers to straight or branched chain lower alkylene groups having from 1 to 6 carbon atoms, i.e., methylene, ethylene, n-propylene, iso propylene, n-butylene, sec-butylene, tert-butylene, 3-methylpentylene, 2-methylbutylene, 1,1-dimethylethylene, and the like.

The term "substituted phenyl" refers to phenyl having one or more substituents selected from the group consisting of halo, hydroxy, phenyl, lower alkyl and lower alkoxy.

The term "aryl" refers to phenyl, naphthyl, and the like.

The term "halo", as used herein in reference to alkyl, cycloalkyl, aryl, and phenyl substituents, includes chloro, bromo, iodo and fluoro.

The term "lower alkoxy" refers to alkoxy groups having from 1 to 6 straight or branched chain carbon atoms, i.e., methoxy, propoxy, tert butoxy, pentoxy, etc.

The term "cycloalkyl" refers to cycloalkyl groups having from 3 to 6 carbon atoms.

The term "substituted cycloalkyl" refers to a cycloalkyl group having one or more substituents selected from the group consisting of halo, hydroxy, lower alkyl and lower alkoxy.

The term "tert-alkyl" as used herein in reference to $R_1$ and $R_2$ refers to branched chain alkyl moieties of from about 4 to 10 carbon atoms having a tertiary carbon atom attached to the phenyl ring substituted by $R_1$ and $R_2$. Examples of such groups are tert butyl, i.e., 1,1-dimethylethyl, 1-1 dimethylpropyl, 1-methyl-1-(ethyl) pentyl, 1,1-diethylpropyl, 1-ethyl-1-(propyl)butyl and the like.

Scheme A illustrates the use of the process of the present invention for the preparation of α alkoxy acetic acids of Formula I in which R is defined as hereinbefore from alcohols of Formula II by: (a) reacting the alcohol (II) with a base such as sodium hydride in an aprotic organic solvent such as tetrahydrofuran (THF) to form an alkoxide (IIa) followed by removal of the organic solvent and coupling of the alkoxide with a salt of a monohaloacetic acid such as sodium monochloroacetate in a polar aprotic solvent such as dimethyl sulfoxide (DMSO) to form the acetate salt (IIb) which is converted to the acid (I) by reaction with an organic acid or a mineral acid such as hydrochloric acid.

Scheme B illustrates the preparation of substituted phenyl-α-alkoxy acetic acids of Formula IV wherein $R^1$, $R^2$, $R^3$, A and Alk are defined as hereinbefore from alcohols of Formula III by the process of the present invention.

Scheme C illustrates the preparation of (3,5-disubstituted-4-hydroxyphenyl)thio-α-alkoxy acetic acids of Formula VI wherein $R^1$, and $R^2$ are alkyl of 1 to 10 carbon atoms, halo, phenyl or substituted phenyl and A and Alk are defined as hereinbefore from alcohols of Formula V by the process of the present invention.

The present invention is particularly useful for preparing (±)[2S*-[[3,5-bis(1,1-dimethylethyl)-4-hydroxyphenyl]thio]-1R*-methylpropoxy]acetic acid (Formula VIII) which is a 5-lipoxygenase inhibiting compound and is useful in the treatment of inflammation, allergy, and hypersensitivity reactions. Scheme D illustrates the preparation of this compound by reacting (±)2,6-bis(1,1-dimethylethyl)-4-[(2S*-hydroxy-1R*-methylpropyl)thio]phenol (Formula VII) with sodium hydride in THF followed by removal of the THF and reaction of the resulting alkoxide with sodium monochloroacetate in DMSO to form the alkoxyacetate salt which is then reacted with hydrochloric acid to give the product. Yields of 90% and greater can be obtained using this process.

U.S. Pat. No. 4,755,523 discloses a method of making the compound of Formula VIII by refluxing the alcohol of Formula VII with chloroacetic acid and potassium tert-butoxide in butanol, adding sodium bicarbonate to make the reaction mixture basic, extracting with ethyl ether than acidifying the extracts with hydrochloric acid to give the product. This process is illustrated in Scheme E. This process gives yields of less than 25% of product.

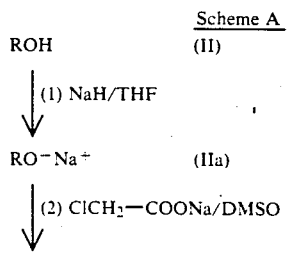

-continued
Scheme A

ROCH₂COO⁻Na⁺ (IIb)

| (3) H⁺
↓

ROCH₂COOH (I)

Scheme B

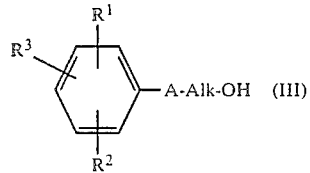

| (1) NaH/THF
| (2) ClCH₂COONa/DMSO
| (3) H⁺
↓

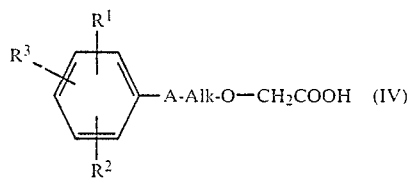

Scheme C

| (1) NaH/THF
| (2) ClCH₂COONa/DMSO
| (3) H⁺
↓

-continued
Scheme C

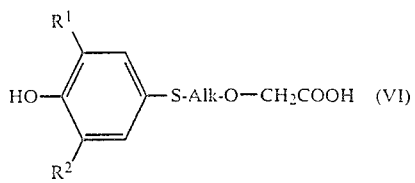

Scheme D

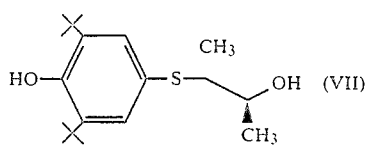

| (1) NaH/THF
| (2) ClCH₂COONa/DMSO
| (3) H⁺Cl⁻
↓

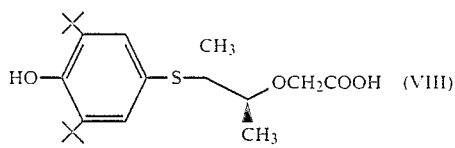

Scheme E

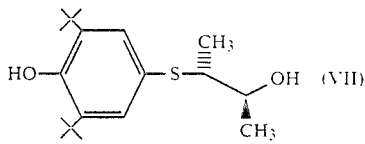

ClCH₂COOH

CH₃   CH₃         CH₃   CH₃
   C              /    C
CH₃   OH        CH₃   O⊖K⊕

↓

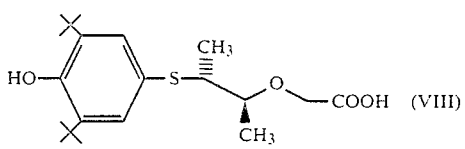

The following examples further illustrate the invention. All temperatures are degrees Celsius unless otherwise noted.

EXAMPLE 1

(±)2,6-Bis(1,1-dimethylethyl)-4-[(2S*-hydroxy-1R*-methylpropyl)thio]phenol

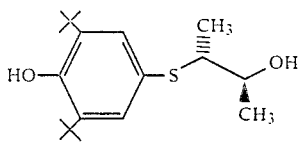

An argon-purged vessel was charged with 54 L of anhydrous methanol which was then purged with argon for 5 min. About 12 L of methanol was distilled off at atmospheric pressure, and the remaining methanol was transferred to pressure cans under argon. The dry, argon purged vessel was charged with 3.03 kg of sodium methoxide followed by 29.7 kg of methanol from the pressure cans. The mixture was stirred for 10 min, and 6.7 kg of 2,6-bis(1,1-dimethylethyl)-4-mercaptophenol was added in small portions under argon. The mixture was stirred for 1 h at room temperature and cooled to 0° C. at which point 2.23 kg of trans-2,3-epoxybutane was added followed by a 2.7 kg methanol rinse. The mixture was stirred at 0° C. for 4 h and then at less than 25° C. for 16 h. When the reaction was complete as indicated by thin layer chromatography, the reaction mixture was added to 59 L of 1N hydrochloric acid, and the agueous solution was extracted twice with a total of 89 L of ethyl acetate. The combined organic phase was washed once with 34 L of dilute agueous sodium chloride solution and once with 13 L of saturated agueous sodium chloride solution. The organic phase wa dried over 3.5 kg of anhydrous magnesium sulfate and filtered. The solvent was removed by distillation under reduced pressure. The crude product was dissolved in 6.7 L of refluxing n hexane, and the solution was cooled to 5° C. The solid was collected by filtration, washed with cold (about 0° C.) n-hexane and dried at 50° C. in a vacuum oven to give 7.44 kg (85% of theory) of (±)2,6 bis(1,1-dimethylethyl)-4-[(2S*-hydroxy-1R*-methylpropyl)thio]phenol.

EXAMPLE 2

(±)[2S* [[3,5-Bis(1,1-dimethylethyl)-4-hydroxyphenyl]thio]-1R*-methylpropoxy]acetic acid

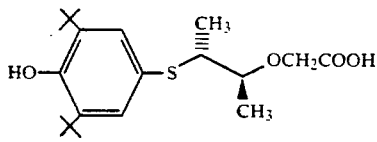

A dry, argon purged vessel was charged with 1.6 kg of sodium hydride (60% dispersion in oil) which was then washed three times with a total of 21 kg of n-heptane. The reaction vessel was cooled to −20° C., and 41 L of dry tetrahydrofuran (THF) was added under argon. A solution of 4.0 kg of (±)2,6-bis(1,1-dimethylethyl)-4-[(2S*-hydroxy- 1R*-methylpropyl) thio]phenol in 16 L of tetrahydrofuran was added slowly to the sodium hydride suspension, and the mixture was warmed to 0–5° C. and stirred for 1.5 h. The tetrahydrofuran was removed at reduced pressure, and 12 L of dimethyl sulfoxide was added under argon. A solution of 1.9 kg of sodium chloroacetate in 40 L of dimethyl sulfoxide was added, and the mixture was stirred at room temperature for approximately 15 h. When the reaction was complete, as indicated by thin layer chromatography, the reaction mixture was added to approximately 178 L of water at 5–10° C., and the aqueous solution was extracted twice with a total of 60 L of n heptane. The agueous phase was acidified with 14 L of 4N hydrochloric acid and extracted three times with a total of 95 L of ethyl acetate. The combined organic phase was washed twice with a total of 74 L of water and once with 20 L of saturated agueous sodium chloride solution. The organic phase was dried over 2.0 kg of anhydrous magnesium sulfate, filtered, and the solvent was removed by distillation under reduced pressure. The product was dissolved in 40 L of refluxing n-hexane, and the solution was cooled to room temperature. The product was collected by filtration, washed twice with a total of 20 L of n hexane and dried at room temperature in a vacuum oven to give 4.27 kg (90% of theory) of (±)[2S*-[[3,5-bis(1,1-dimethyl-ethyl)-4-hydroxyphenyl]thio]-1R*-methylpropoxy]acetic acid (first crop). The hexane filtrate was concentrated under vacuum to give an additional 0.23 kg of product (4.80% of theory).

EXAMPLE 3

2-Methylpropoxyacetic acid

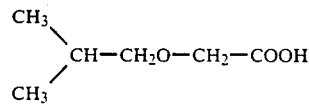

Sodium hydride (1.72 g of 60% NaH in oil=1.03 g, 43 mmol) in oil dispersion was washed twice with 10 ml of hexane. THF was added (10 ml) and the mixture was cooled to −15° C. A solution of 2-methyl propanol (2.5 g, 35 mmol) in THF was then added, and the mixture was warmed to 25° C. for 1 hour. The THF was removed by distillation under vacuum and a solution of sodium chloroacetate (5.2 g, 45 mmol) in DMSO (100 ml) was added. The mixture was stirred at room temperature for 20 hours, then diluted with 300 ml. of water. The mixture was extracted twice with 50 ml. of hexane. The agueous phase was acidified with 4 N hydrochloric acid and the product was extracted twice with 100 ml. of ethyl acetate. The combined ethyl acetate layers were washed twice with 100 ml. water, dried over MgSO₄, filtered, and the solvent was removed by distillation under reduced pressure to give 4.6g of product as a colorless oil. Yield of product=99.6%.

EXAMPLE 4

Cyclohexyloxy acetic acid

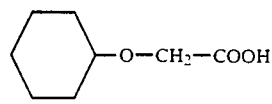

Using the procedure of Example 3, 0.86 g of a 60% dispersion of sodium hydride in oil (0.516 g, 21.5 mmol) was washed twice with hexane. THF (5 ml) was added, and the mixture was cooled to −15° C.

A solution of cyclohexanol (1.75 g, 17.5 mmol) in THF was added, and the mixture was warmed to 25° C. for 1 hour. The THF was removed by distillation under vacuum, and a solution of sodium chloroacetate (2.5 g, 22 mmol) in DMSO (50 ml) was added. The reaction mixture was treated as in Example 3 and 2.3 g of product (83% yield) was obtained as a colorless oil.

EXAMPLE 5

[2R*-[[3,5-Bis(1,1-dimethylethyl)-4-hydroxyphenyl]thio]-1R*-methylpropoxy]acetic acid

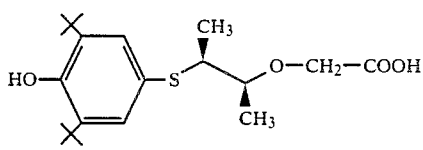

Sodium hydride (6 g of a 60% dispersion in oil=3.6 g, 0.15 mole) under argon was washed twice with 3 ml heptane then 150 ml of distilled THF was added and the mixture was cooled to −20° C. and a solution of 15 g of 2,6-Bis(1,1-dimethylethyl)-4-[(2R* -hydroxy-1R*-methylpropyl)thio]phenol (15 g, 0.048 mole) (prepared as in Example 1 using cis-2,3-epoxybutane instead of trans 2,3-epoxybutane) in 70 ml of THF was added. The reaction mixture was stirred at 0° C. for 1 hour and the THF was removed under vacuum. DMSO (45 ml) was added. A mixture of sodium chloroacetate (7.2 g) in 150 ml DMSO was added and the addition flask was rinsed with 30 ml of DMSO. The reaction mixture was stirred at room temperature for 17 hours. The solution was diluted with 150 ml of water and extracted twice with 50 ml hexane. The agueous layer was acidified with 20 ml 4N HCl. The mixture was extracted twice with 100 ml ethyl acetate, and the combined ethyl acetate extractions were washed with 100 ml water and 50 ml saturated sodium chloride and dried over magnesium sulfate overnight. Filtration and removal of the solvent gave 17.8 g of product as a pale yellow oil (91% yield).

What is claimed is:

1. A process for preparing a compound of the formula $$RO-CH_2COOH \quad (I)$$

or a salt thereof, wherein R is straight or branched chain alkyl, substituted alkyl having one or more substituents selected from the group consisting of alkoxy, cycloalkyl, aryloxy, arylthio, phenyl, and, substituted phenyl having one or more substituents selected from the group consisting of halo, hydroxy, phenyl, lower alkyl, and lower alkoxy, cycloalkyl, substituted cycloalkyl having one or more substituents selected from the group consisting of halo, hydroxy, lower alkyl and lower alkoxy, cycloalkyl substituted cycloalkyl alkyl wherein the cycloalkyl is substituted by one or more substituents selected from the group consisting of halo, hydroxy, lower alkyl, and lower alkoxy, or a group of the formula

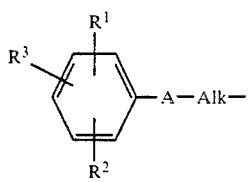

wherein $R^1$, $R^2$ and $R^3$ can be the same or different and can be hydrogen, alkyl of 1 to 10 carbon atoms, lower alkoxy, halo, phenyl, substituted phenyl having one or more substituents selected from the group consisting of halo, hydroxy, phenyl, lower alkyl and lower alkoxy, or hydroxy; A can be sulfur, oxygen, or —CH$_2$—; and Alk can be straight or branched chain lower alkylene; which comprises:

(a) reacting a compound of the formula

R—OH wherein R is defined as hereinbefore with a base in an aprotic organic solvent to form an alkoxide;

(b) removing the organic solvent;

(c) reacting the alkoxide with a salt of a monohaloacetic acid in an aprotic polar solvent to give an alkoxyacetate salt; and (d) optionally reacting the alkoxyacetate salt with an acid.

2. A process according to claim 1 for preparing a compound of the formula

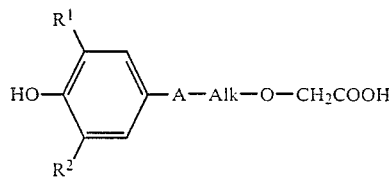

or a salt thereof wherein $R^1$ and $R^2$ are the same or different and are tert-alkyl of 4 to 10 carbon atoms, halo, phenyl, or substituted phenyl having one or more substituents selected from the group consisting of halo, hydroxy, phenyl, lower alkyl and lower alkoxy; A is sulfur, oxygen, or —CH$_2$—; and Alk is straight or branched chain alkylene having 1 to 6 carbon atoms; which comprises:

(a) reacting a compound of the formula

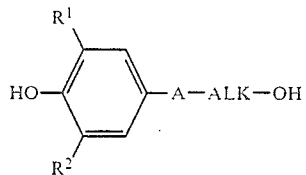

wherein, $R^1$, $R^2$, A, and Alk are defined as hereinbefore, with a base in an aprotic organic solvent to form an alkoxide;

(b) removing the organic solvent;

(c) reacting the alkoxide with a salt of a monohaloacetic acid in an aprotic polar solvent to give an alkoxyacetate salt; and (d) optionally reacting the alkoxyacetate salt with an acid.

3. A process according to claim 2 wherein A is sulfur.

4. A process according to claim 2 wherein $R^1$ and $R^2$ are tert-alkyl.

5. A process according to claim 4 wherein $R^1$ and $R^2$ are tert-butyl.

6. A process according to claim 2 wherein $R^1$ and $R^2$ are phenyl or substituted phenyl having one or more substituents selected from the group consisting of halo, hydroxy, phenyl, lower alkyl, and lower alkoxy.

7. A process according to claim 2 wherein $R^1$ and $R^2$ are halo.

8. A process according to claim 1 wherein the aprotic organic solvent is tetrahydrofuran and the aprotic polar solvent is dimethyl sulfoxide.

9. A process according to claim 2 wherein the aprotic organic solvent is tetrahydrofuran and the aprotic polar solvent is dimethyl sulfoxide.

10. A process according to claim 8 wherein the salt of a monohaloacetic acid is sodium chloroacetate.

11. A process according to claim 9 wherein the salt of a monohaloacetic acid is sodium chloroacetate.

12. A process according to claim 11 wherein the base is sodium hydride.

13. A process according to claim 2 for preparing a compound of the formula

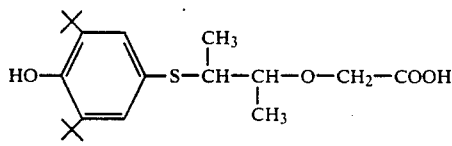

which comprises:
(a) reacting an alcohol of the formula

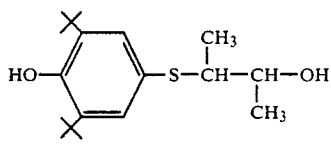

with a base in an aprotic organic solvent to form an alkoxide;
(b) removing the organic solvent;
(c) reacting the alkoxide with a salt of a monohaloacetic acid in an aprotic polar solvent to form an alkoxyacetate salt; and
(d) reacting the alkoxyacetate salt with an acid.

14. A process according to claim 13 wherein the aprotic solvent is tetrahydrofuran and the polar aprotic solvent is dimethyl sulfoxide.

15. A process according to claim 14 wherein the salt of a monohaloacetic acid is sodium chloroacetate.

16. A process according to claim 13 for preparing a compound of the formula

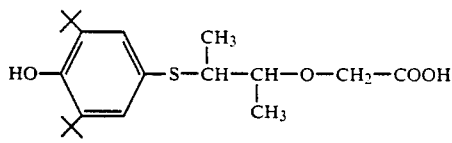

which comprises:
(a) reacting an alcohol of the formula

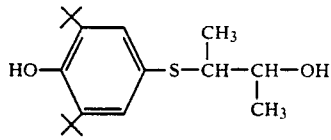

with sodium hydride in tetrahydrofuran to form an alkoxide;
(b) removing the tetrahydrofuran;
(c) reacting the alkoxide with sodium chloroacetate in dimethyl sulfoxide to form an alkoxyacetate salt; and
(d) reacting the alkoxyacetate salt with a mineral acid.

17. A process according to claim 13 for preparing a compound of the formula

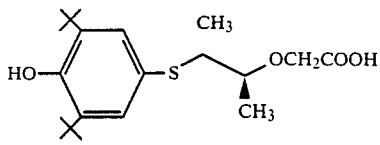

which comprises:
(a) reacting an alcohol of the formula

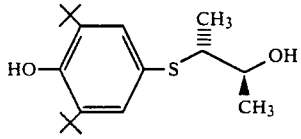

with a base in an aprotic organic solvent to form an alkoxide;
(b) removing the organic solvent;
(c) reacting the alkoxide with a salt of a monohaloacetic acid in a polar aprotic solvent to form an alkoxyacetate salt; and
(d) reacting the alkoxyacetate salt with an acid.

18. A process according to claim 17 wherein the base is sodium hydride.

19. A process according to claim 17 wherein the aprotic organic solvent is tetrahydrofuran.

20. A process according to claim 17 wherein the salt of a monohaloacetic acid is sodium chloroacetate.

21. A process according to claim 17 wherein the polar aprotic solvent is dimethyl sulfoxide.

22. A process according to claim 17 for preparing a compound of the formula

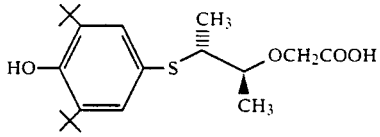

which comprises:
(a) reacting an alcohol of the formula

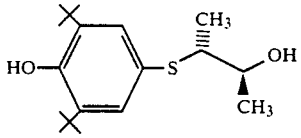

with sodium hydride in tetrahydrofuran to form an alkoxide;
(b) removing the tetrahydrofuran;
(c) reacting the alkoxide with sodium chloroacetate in dimethyl sulfoxide to form an alkoxyacetate salt; and
(d) reacting the alkoxyacetate salt with an acid.

23. A process according to claim 22 wherein the acid is hydrochloric acid.

24. A process according to claim 1 wherein R is substituted alkyl having one or more substituents selected from the group consisting of alkoxy, cycloalkyl, phenyl, phenylthio, phenyloxy, and substituted phenyl having one or more substituents selected from the group consisting of halo, hydroxy, phenyl, lower alkyl and lower alkoxy.

* * * * *

UNITED STATES PATENT AND TRADEMARK OFFICE
CERTIFICATE OF CORRECTION

PATENT NO.  : 5,013,864                             Page 1 of 3
DATED       : May 7, 1991
INVENTOR(S) : Campbell, et. al.

It is certified that error appears in the above-identified patent and that said Letters Patent is hereby corrected as shown below:

Column 1, line 64, reading "in an agueous alkaline" should read -- in an aqueous alkaline --.

Column 4, line 21, reading "or Salt" should read -- or salt --.

Column 5, line 24, reading "The reactiOn" should read -- The reaction --.

Column 6, line 49, reading " U.S. Pat.No. 4,755,523" should read -- U.S. Pat. No. 4,755,524 --.

Column 8, Scheme D, reading

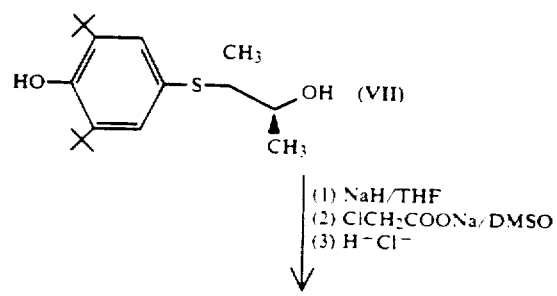

should read

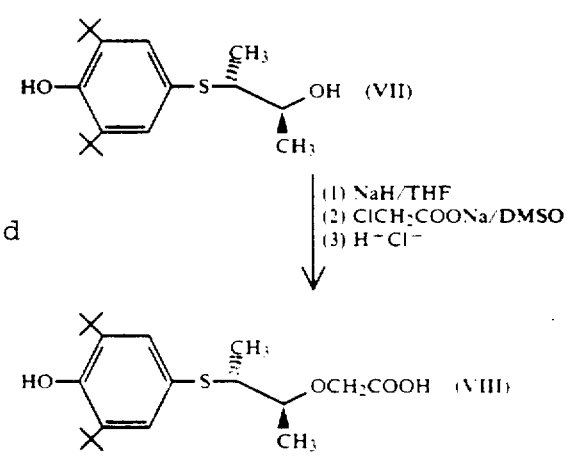

UNITED STATES PATENT AND TRADEMARK OFFICE
CERTIFICATE OF CORRECTION

PATENT NO. : 5,013,864  
DATED : May 7, 1991  
INVENTOR(S) : Campbell et al.

It is certified that error appears in the above-identified patent and that said Letters Patent is hereby corrected as shown below:

Column 9, line 16, reading "the agueous" should read -- the aqueous --.

Column 9, line 18, reading "dilute agueous" should read -- dilute aqueous --.

Column 9, line 19, reading "saturated agueous" should read -- saturated aqueous --.

Column 9, line 20, reading "The organic phase wa dried" should read -- The organic phase was dried --.

Column 9, line 60, reading "the agueous" should read -- the aqueous --.

Column 9, line 62, reading "The agueous" should read -- The aqueous --.

Column 9, line 66, reading "saturated agueous sodium" should read -- saturated aqueous sodium --.

Column 10, line 37, reading "The agueous phase" should read -- The aqueous phase --.

Column 11, line 28, reading "The agueous layer" should read -- The aqueous layer --.

UNITED STATES PATENT AND TRADEMARK OFFICE
CERTIFICATE OF CORRECTION

PATENT NO. : 5,013,864

DATED : May 7, 1991

INVENTOR(S) : Campbell, et. al.

It is certified that error appears in the above-identified patent and that said Letters Patent is hereby corrected as shown below:

Claim 17, Line 5, the structure reading

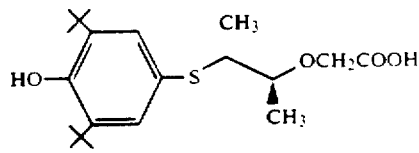

should read

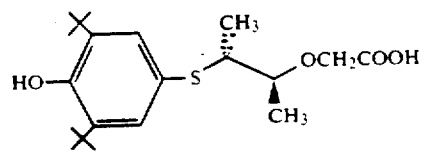

Signed and Sealed this

Sixth Day of July, 1993

*Attest:*

MICHAEL K. KIRK

*Attesting Officer*  Acting Commissioner of Patents and Trademarks